US009469842B2

(12) United States Patent
Kim et al.

(10) Patent No.: US 9,469,842 B2

(45) Date of Patent: Oct. 18, 2016

(54) KOREAN-TYPE PORCINE REPRODUCTIVE AND RESPIRATORY SYNDROME (PRRS) VIRUS

(71) Applicant: OPTIPHARM CO., LTD, Cheongwon-gun (KR)

(72) Inventors: Hyun Il Kim, Seongbuk-gu (KR); Seong Ho Shin, Cheongwon-gun (KR); Beom Ku Han, Seo-gu (KR)

(73) Assignee: OPTIPHARM CO., LTD., Chungcheongbukdo (KR)

( * ) Notice: Subject to any disclaimer, the term of this patent is extended or adjusted under 35 U.S.C. 154(b) by 0 days.

(21) Appl. No.: 14/778,900

(22) PCT Filed: Feb. 3, 2014

(86) PCT No.: PCT/KR2014/000897

§ 371 (c)(1),
(2) Date: Sep. 21, 2015

(87) PCT Pub. No.: WO2014/148738

PCT Pub. Date: Sep. 25, 2014

(65) Prior Publication Data

US 2016/0076005 A1 Mar. 17, 2016

(30) Foreign Application Priority Data

Mar. 20, 2013 (KR) ........................ 10-2013-0029891

(51) Int. Cl.

| | |
|---|---|
| ***C12N 7/00*** | (2006.01) |
| ***A61K 39/12*** | (2006.01) |
| ***G01N 33/569*** | (2006.01) |
| *A61K 39/00* | (2006.01) |

(52) U.S. Cl.

CPC ................. *C12N 7/00* (2013.01); *A61K 39/12* (2013.01); *G01N 33/56983* (2013.01); *A61K 2039/525* (2013.01); *A61K 2039/54* (2013.01); *A61K 2039/543* (2013.01); *C12N 2770/10021* (2013.01); *C12N 2770/10034* (2013.01); *G01N 2333/08* (2013.01); *G01N 2469/20* (2013.01)

(58) Field of Classification Search

None

See application file for complete search history.

(56) References Cited

PUBLICATIONS

Kim et al. Virology Journal 2011, vol. 8, 6 pages.*

Allende, R. and Other, North American and European porcine reproductive and respiratory syndrome viruses differ in non-structural protein coding regions; Journal of General Virology (1999), 80, 307-15. Printed in Great Britain.

Andrerev, V.G. and Others, Genetic variation and phylogenetic relationships of 22 porcine reproductive and respiratory syndrome virus (PRRSV) field strains based on sequence analysis of open reading frame 5; Archives of Virology (1997) 142, 993-1001. Springer-Verlag, Printed in Austria.

Bastos R.G. and Others, Immune response of pigs inoculated with *Mycobacterium bovis* BCG expressing a truncated form of GP5 and M protein of porcine reproductive and respiratory syndrome virus; Vaccine (2004) 22, 467-74, Elsevier.

Benfield, D.A. and Others, Characterization of swine infertility and respiratory syndrome (SIRS) virus (isolate ATCC VR-2332); Journal of Veterinary Diagnostic Investigation (1892) 4, 127-33.

Brierley, I. and Others, Characterization of an Efficient Coronavius Ribosomal Frameshifting Signal: Requirement for an RNA Pseudoknot; Cell (1989) 57, 537-47. Cell Press.

Cavanagh, D. Nidovirales: a new order comprising Coronaviridae and Arteriviridae; Archives of Virology (1997) 142/3, 629-33; Printed in Austria.

Collins, J. E. and Others; Isolation of swine infertility and respiratory syndrome virus (isolate ATCC VR-2332) in North America and experimental reproduction of the disease in gnotobiotic pigs; Journal of Veterinary Diagnostic Investigation (1992)4, 117-26.

Gagnon, G,A. and Dea, S. Differentiation between Porcine Reproductive and Respiratory Syndrome Virus Isolates by Restriction Fragment Length Polymorphism of Their ORFs 6 and 7 Genes; Canadian Journal of Veterinary Research (1998) 62, 110-16.

Halbur, P.G. and Others, Experimental Disearse: Comparison of the Pathogenicity of Two US Porcine Reproductive and Respiratory Syndrome Virus Isolates with that of the Lelystad Virus; Veterinary Pathology (1995) 32, 648-60.

Halbur, P.G. and Others, Comparson of the Antigen Distribution of Two US Porcine Reproductive and Respiratory Syndrome Virus Isolates with that of the Lelystad Virus; Veterinary Pathology (1996) 33, 159-70.

Kwang J. and Others, Cloning, expression, and sequence analysis of the ORF4 gene of the porcine reproductive and respiratory syndrome virus MN-1b; Journal of Veterinary Diagnostic Investigation (1994) 6, 293-96.

(Continued)

*Primary Examiner* — Shanon A Foley

*Assistant Examiner* — Myron Hill

(74) *Attorney, Agent, or Firm* — Weisun Rao; Fang Xie; Greenberg Traurig, LLP

(57) ABSTRACT

The present invention relates to a Korean-type porcine reproductive and respiratory syndrome virus (PRRSV) and a vaccine composition using the same, and a method for preventing porcine reproductive and respiratory syndrome. Korean-type porcine reproductive and respiratory syndrome virus with accession number KCTC 12096BP according to the present invention is Korean-type porcine reproductive and respiratory syndrome virus distinguished from European strains and North American strains, and a vaccine composition specific to Korean-type porcine reproductive and respiratory syndrome virus is produced, thereby preventing a Korean-type porcine reproductive and respiratory syndrome virus or specifically diagnosing the infection with Korean-type porcine reproductive and respiratory syndrome virus.

11 Claims, 5 Drawing Sheets

(56) References Cited

PUBLICATIONS

Meulenberg, J.J.M. and Others, Subgenomic RNAs of Lelystad virus contain a conserved leader-body junction sequence; Journal of General Virology (1993) 74, 1697-1701. Print in Great Britain.

Meulenberg, J.J.M. and Others, Chaacerzaton of Poeins Encoded by ORFs 2 to 7 of Lelystad Virus; Virology (1995) 206, 155-163. American Press, Inc.

Murtaugh, M.P. and Others, Comparison of the structural protein coding sequences of the VR-2332 and Lelystad virus strains of the PRRS virus; Archives of Virology (1995) 140, 1451-60. Springer-Verlag, Printed in Austria.

Meulenberg, J.J.M. and Others, Identification of a Novel Structural Protein of Arteriviruses; Journal of Virology (1999) vol. 73 No. 8, 6335-45. American Society for Microbiology.

Ward, C.D. and Others, Direct Measurement of the Poliovirus RNA Polymerase Error Frequency In Vitro: Journal of Virology (1988) vol. 62 No. 2, 558-62. American Society for Microbiology.

Wootton, S.K. and Others, Antigenic Structure of the Nucleocapsid Protein of Porcine Reproductive and Respiratory Syndrome Virus; Clinical and Diagnostic Laboratory Immunology (1998) vol. 5 No. 6, 773-79. American Society for Microbiology.

* cited by examiner

DRAWINGS a) Total white blood cell

*Normal range(11.0~22.0 k/ μℓ)

b) lymphocyte

*Normal range(4.3~13.6 k/ μℓ)

KOREAN-TYPE PORCINE REPRODUCTIVE AND RESPIRATORY SYNDROME (PRRS) VIRUS

CROSS REFERENCE TO RELATED APPLICATIONS

This application is a national phase filing under 35 U.S.C. 371 of International Application No. PCT/KR2014/000897 filed Feb. 3, 2014, which claims priority to and the benefit of Korean Application No. KR 10-2013-0029891 filed Mar. 20, 2013, the disclosure of each of which applications is incorporated herein by reference in its entirety.

FIELD OF THE INVENTION

The present invention relates to a Korean-type porcine reproductive and respiratory syndrome virus (PRRSV) and a vaccine composition using the same, and a method for preventing porcine reproductive and respiratory syndrome.

DESCRIPTION OF THE RELATED ART

In 1987, the occurrence of a novel porcine disease from an unknown cause began to be reported around the swine raising region in U.S.A. This disease which expresses reproductive disorders and respiratory infections complexly explosively increased in summer in 1988 and 1989. Initially, this disease, which suddenly emerged and caused massive damages to the US swine industry, was called swine mysterious disease, and thereafter, as a causative virus was isolated and studies on clinical symptoms, pathogenicity, etc. progressed, at present, this disease is internationally named PRRS (Porcine Reproductive and Respiratory Syndrome) according to the characteristics of the clinical symptoms which express both reproductive disorders and respiratory infections.

In Korea, although no prevalence of symptoms similar to this disease was reported, since 1992, studies on this disease started to establish diagnostics thereof, and epidemiological investigation for Korean swine farms was conducted, and as a result, it was confirmed that this disease was also introduced in Korea, and a causative virus was isolated from Korean infected farms. In Asia, the confirmation of the occurrence and the isolation of the causative virus were reported in Japan and Taiwan other than Korea.

Even after the report of the occurrence, the exact cause was unknown, so the swine industry got into great confusion. In June, 1991, Dr. Wensvoort at the Netherlands Central Veterinary Laboratory isolated the causative virus using porcine alveolar macrophage for the first time. This virus was named Lelystad virus according to the place name where the Netherlands Central Veterinary Laboratory was located, and soon afterwards, causative virus was isolated in many countries including U.S.A. As a result of the investigation on its properties and pathogenicity, etc., it was discovered that the novel porcine disease, which resulted in reproductive disorders and respiratory infections complexly in U.S.A. and Europe so far, was caused by this virus.

PRRS virus which is often called Lelystad virus in Europe and SIRS virus in U.S.A has an outer membrane, and this virus is a small globular virus having a diameter of 45-80 mm, and there are small processes on its surface. On a site where genes are present, a single-chain RNA gene having a diameter of 25-35 nm is located. Since this virus is not so strong on an external environment, at acidity of less than 5 or higher than 7, the virus infection titer is reduced by 90% or more, and after 10 to 24 hours at 37° C. and after 6 days at 20° C., the infection titer is reduced more than 10 times. When pigs are inflected with this virus, cases causing a disease are very various, including cases where there are no clinical symptoms and no economic damages such that the inflection can be detected only by a serum test, and serious cases such that it causes 20% of loses in the production of farms.

As can be known from the disease name, reproductive disorders and respiratory diseases are expressed complexly. The characteristics of reproductive disorders caused by PRRS virus inflection are miscarriage in the late stage of pregnancy or premature farrowings concentrated between 107 days and 113 days of pregnancy, the occurrence of stillborn and mummified pigs, sudden increase in mortality rate before weaning pigs, increase in mortality rate after weaning, delayed return to estrus, etc. These symptoms intensively appear in infected sows and pigs born from the sows. It has been known that reproductive disorders caused by PRRS virus infection are almost recovered to its pre-infection state after about 6 months from the early stage of the inflection. Respiratory diseases caused by PRRS virus infection may appear in all ages, and in particular, the diseases intensively appear in suckling pigs and weaning pigs. In this case, fast abdominal breathing is observed, and palpebral edema, conjunctivitis, sneeze, diarrhea, etc. are observed, and there is a case where body temperature increases for a short period, and neurological sign and symptom may rarely appear. The respiratory diseases are mainly caused by a secondary infection and a complex infection with bacillary, viral pathogenic organisms, rather than by an infection with virus alone, and in this case, pathogenicity is much higher. Other than the above, there are cases where locus caeruleus may occur on ears, abdomen, pudenda, etc., so in the United Kingdom, this disease is also called Blue ear disease.

The aforementioned clinical symptoms can be apparently observed when the disease proceeds acutely, and distinct and characteristic clinical symptoms can be rarely observed when the disease is caused by a subclinical infection or proceeds chronically. Chronic infections mainly spread in weaning pigs and growing-fattening stage, and respiratory systems which receive attacks by PRRS virus are infected with germ and virus, which results in rhinitis and pneumonia. Consequently, an average daily weight gain is lowered, the feed conversion rate increases much more, and the mortality rate after weaning increases twice than the average mortality rate before the infection with PRRS virus. Lung suffering from a respiratory disease caused by PRRS virus expresses pathologically characteristic epileptic pneumonitis.

As PRRS virus, currently, Lelystad virus (Wensvoort et al., 1991) which was first isolated in Europe and VR-2332 [0004] Virus (Benfield et al., 1992) which was isolated in North America are classified as prototypes of European strains and North American strains, respectively, and their sequence homology is about 50 to 70%, which is very low (Gagnon and Dea, 1998; Kwang et al., 1994; Murtaugh et al., 1995). Currently, PRRS virus, together with equine arthritis virus (EAV), lactate dehydrogenase-elevating virus (LDV) and simian hemorrhagic fever virus (SHFV), belongs to order Nidovirales, and family Arteriviridae (Cavanagh, 1997). PRRS virus, which is a very small enveloped virus having phosphatides, has single strain RNA genome with about 15 kb of positive-polarity in the regular polyhedron shaped nucleocapsid (Collins et al., 1992). Genes encoding replicase, which is a unstructured protein consisting of enzymes necessary for autoreplication of virus, occupy about 80% from 5'-terminal of genomic RNA, and they are generated by ORF1a and ORF1b having an overlapping site expressed from genomic RNA. Out of them, ORF1b has been reported to be expressed by the ribosomal frameshift mechanism (Brierley et al., 1989). Structured proteins of virus occupy about 20% from 3'-terminal of genomic RNA, and they are expressed from 7 genes, i.e. from ORF2a, ORF2b to ORF7. ORF2, ORF3 and ORF4 generate glycosylated membrane proteins which are GP2, GP3 and GP4, respectively. ORF5 generates glycoprotein GP5 envelope protein, which plays the most important role in PRRS virus neutralization activity. ORF6 generates M (matrix), and ORF7 generates N (nucleocapside) (Meulenberg et al., 1995; Bastos et al., 2004). They are expressed from 5'-terminal of monocistronic subgenomic mRNA in infected cells (Meulenberg et al., 1993; Synder et al., 1999). Study results on the function and molecular biological characteristics of most of proteins including unstructured proteins as well as structured proteins of PRRS virus are still insufficient. When pigs are infected with PRRS virus, serious reproductive disorders and respiratory disorders are expressed as clinical symptoms. Despite the fact that it cannot be proven that PRRS virus European strains and North American strains are distinctly different in symptoms of the diseases, they have distinct antigenical or genotype difference (Allende et al., 1999; Halbur et al., 1995; Wootton et al., 1998). In addition, in North American strains and European strains, there is a difference between isolated strains. For example, it has been reported that variants of base sequences among several isolated strains belonging to North American strains may be caused by an essential error of RNA polymerase or RNA recombinant, and genetic variant thereof may lead to an important difference in pathogenicity of virus (Andreyev et al., 1997; Halbur et al., 1996; Ward et al., 1988).

However, a vaccine suitable for Korean variants by isolating Korean-type PRRSV and the preparation method of Korean-type PRRSV using the same have not been commercialized yet. Therefore, studies on vaccines suitable for Korean-type PRRSV are needed.

SUMMARY OF THE INVENTION

The present inventors conducted the studies by isolating a porcine reproductive and respiratory syndrome virus (hereinafter, PRRSV) from Korean pigs and found that the isolated virus was a novel Korean-type PRRSV, and then completed the present invention.

The object of the present invention is to provide a novel Korean-type PRRSV, a vaccine composition using the same, and a method for preventing porcine reproductive and respiratory syndrome.

In order to achieve the above object, the present invention provides a Korean-type porcine reproductive and respiratory syndrome virus (hereinafter, PRRSV) (Accession Number KCTC 12096BP).

In addition, the present invention provides a vaccine composition comprising a Korean-type porcine reproductive and respiratory syndrome virus (Accession Number KCTC 12096BP) as an effective ingredient.

In addition, the present invention provides a method for preventing porcine reproductive and respiratory syndrome, comprising administering the virus vaccine composition to a pig.

In addition, the present invention provides a diagnosis kit for a Korean-type porcine reproductive and respiratory syndrome virus, comprising a Korean-type porcine reproductive and respiratory syndrome virus (Accession Number KCTC 12096BP) or an antigen thereof.

In addition, the present invention provides a method for detecting a Korean-type porcine reproductive and respiratory syndrome virus, characterized by detecting a Korean-type porcine reproductive and respiratory syndrome virus (Accession Number KCTC 12096BP) in a cell to be infected or being infected through an antigen-antibody reaction using a Korean-type porcine reproductive and respiratory syndrome virus (Accession Number KCTC 12096BP) or an antigen thereof.

Korean-type porcine reproductive and respiratory syndrome virus with Accession Number KCTC 12096BP according to the present invention is a Korean-type porcine reproductive and respiratory syndrome virus distinguished from European strains and North American strains, and a vaccine composition specific to the Korean-type porcine reproductive and respiratory syndrome virus which is capable of preventing the Korean-type porcine reproductive and respiratory syndrome or specifically diagnosing the infection with Korean-type porcine reproductive and respiratory syndrome virus can be produced.

BEST MODE FOR CARRYING OUT THE INVENTION

Figure 1:
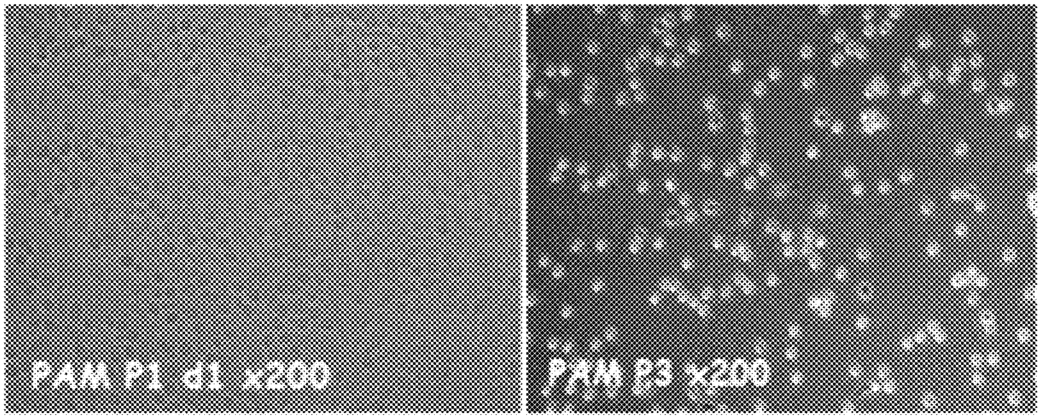
FIG. 1 is a diagram showing porcine alveolar macrophage isolated from a germ-free pig ($2\times10^8$ cells/ml).

The present invention provides a Korean-type porcine reproductive and respiratory syndrome virus (hereinafter, PRRSV) (Accession Number KCTC 12096BP).

The Korean-type porcine reproductive and respiratory syndrome virus (hereinafter, JW-PRRSV) (Accession Number KCTC 12096BP), which is isolated from outdoor farms, is capable of proliferation in monkey kidney cell, MARC-145 cell, or porcine alveolar macrophage (PAM) which is directly isolated from pigs and cultured, but this virus can be proliferated in any of proliferable cells or mediums without limitation thereto.

In addition, the present invention provides a vaccine composition including JW-PRRSV (Accession Number KCTC 12096BP) as an effective ingredient.

The vaccine composition may include JW-PRRSV which is obtained by culturing JW-PRRSV for 3 to 120 passages. The number of passages is not limited if the activity of this virus can remain, but the vaccine composition may preferably include, as an effective ingredient, JW-PRRSV which is obtained by culturing JW-PRRSV for 3 passages, 5 passages, 91 passages and 120 passages.

The Korean-type porcine reproductive and respiratory syndrome virus (JW-PRRSV) according to the present invention can induce the virus protection equivalent to commercial MLV vaccine, as the result of the formation of the antibody titer and analysis of clinical symptoms. Therefore, this virus may effectively be a novel vaccine candidate substance against the porcine reproductive and respiratory syndrome virus. Further, the Korean-type porcine reproductive and respiratory syndrome virus (JW-PRRSV) according to the present invention does not lead to an inflammatory response in individuals when inoculation, and exhibits safety with no side effects such as suppuration, necrosis, fever, etc. in an injection site. Also, as the virus shedding time is reduced as compared to existing PRRSV vaccines, the problem of the existing PRRSV vaccines can be improved. Therefore, this virus can be useful as a vaccine composition for a novel Korean-type porcine reproductive and respiratory syndrome virus.

The "vaccine" is a veterinary vaccine including an antigen substance. This vaccine is specific to the porcine reproductive and respiratory syndrome and administered for the purpose of inducing active or passive immunity.

The vaccine composition may include one or more suitable adjuvants, excipients or carriers, in addition to an effective ingredient, JW-PRRSV (Accession Number KCTC 12096BP).

A further ingredient which enhances an immune reaction may be constructs often called adjuvants, for example, assistant molecules, for example, but is not limited to interferon, interleukin or growth factor, which are added in for example, aluminum hydroxide, mineral oil or other oil or vaccine or generated by the body after inducing by such further ingredient.

Adjuvant used in the present invention includes a substance which enhances an immune reaction of an injected animal. A variety of different adjuvants have been known in this technical field. Examples of adjuvant used in the present invention may include complete and incomplete freunds adjuvants, vitamin E, nonionic blocking polymers, muramyl dipeptide, Quil A, mineral oil and non-mineral oil, and carbopol. As a preferred example, the vaccine according to the present invention may include a water-in-oil emulsion adjuvant.

Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral carriers include sodium chloride solution, Ringer's dextrose, dextrose and sodium chloride, lactated Ringer's or fixed oils. Intravenous carriers include fluid and nutrient replenishers, electrolyte replenishers such as those based on Ringer's dextrose, and the like. Preservatives and other additives may also be present, such as, for example antimicrobials, antioxidants, chelating agents, inert gases and the like. Preferred preservatives include formalin, thimerosal neomycin, polymyxin B and amphotericin B.

In addition, the vaccine according to the present invention may include one or more suitable emulsifiers, such as Span or Tween.

In addition, the vaccine composition according to the present invention may include protective agents, and any protective agents known in this technical field can be used without limitation. Protective agents may preferably lactose (LPGG) or threhalose (TPGG), and more preferably threhalose.

In addition, the present invention provides a method for preventing porcine reproductive and respiratory syndrome using JW-PRRSV, including administering the JW-PRRSV vaccine composition to a pig.

The method of administering the vaccine composition to a pig may be performed by typical vaccine administration methods, and the administration can be performed through enteral or parenteral path, oral, intranasal, intravenous, intramuscular, subcutaneous, endermic or other suitable path, but are not limited thereto. Preferably, the composition may be inoculated intramuscularly or intranasally.

The vaccine composition preferably includes $2\times10^5$ to $2\times10^7$ PFU/ml of a Korean-type porcine reproductive and respiratory syndrome virus.

In addition, the present invention provides a diagnosis kit for a Korean-type porcine reproductive and respiratory syndrome virus including Korean-type porcine reproductive and respiratory syndrome virus (Accession Number KCTC 12096BP) or an antigen thereof. The diagnosis kit can be produced according to the methods typically used in this technical field.

The diagnosis kit includes tools, reagents, etc. generally used in this technical field for immunologic analysis as well as for Korean-type porcine reproductive and respiratory syndrome virus (Accession Number KCTC 12096BP). These tools/reagents include but are not limited to suitable carriers, markers capable of generating detectable signals, solvents, detergents, buffers, stabilizer, and the like. If a marker is an enzyme, it may include a substrate and a reaction stop stopping agent which are capable of measuring the enzyme activity. Suitable carriers include but are not limited to soluble carriers such as physiologically acceptable buffers known in this technical field, such as PBS, insoluble carriers such as polystyrene, polyethylene, polypropylene, polyacrylonitrile, fluoride resin, crosslinking textrane, polysaccharide, polymer such as magnetic particles where metal is plated on latex, other paper, glass, metal, agarose, and a combination thereof.

In addition, the present invention provides a method for detecting a Korean-type porcine reproductive and respiratory syndrome virus, characterized by detecting a Korean-type porcine reproductive and respiratory syndrome virus (Accession Number KCTC 12096BP) in a cell to be infected or being infected through an antigen-antibody reaction using Korean-type porcine reproductive and respiratory syndrome virus (Accession Number KCTC 12096BP) or an antigen thereof.

The antigen-antibody reaction can be analyzed using tissue immunity staining, radio immunoassay (RIA), enzyme immunoassay method (ELISA), Western Blotting, Immunoprecipitation Assay, Immunodiffusion Assay, Complement Fixation Assay, FACS, protein chip, etc., but they are not limited thereto.

Hereinafter, the present invention will be explained in detail by examples. However, the following examples are just examples of the present invention, and the contents of the present invention are not limited by the following examples.

EXAMPLE 1

Isolation of Korean-Type Porcine Reproductive and Respiratory Syndrome Virus 1.1 Isolation of Porcine Alveolar Macrophage (Hereinafter, PAM)

For a pig used for the isolation of PAM cells to proliferate virus to be isolated, a germ-free pig being 4 to 8 weeks old (Optifarm-Medipig) which was raised in this company's SPF breeding environment was used. After anesthetizing the pig, the entire lung tissue including the lung bronchus was carefully separated such that the tissue was not injured. An injection tube was connected inside of the bronchus of the lung, and a prepared phosphate buffer solution (pH 7.2) was injected into the lung tissue through the bronchus of the lung. Upon confirmation of the expansion of the lung tissue, the phosphate buffer solution in the lung tissue was collected by tilting the insertion tube, and the collected phosphate buffer solution was centrifuged to precipitate cells and suspended in a medium in which prepared 10% fetal bovine serum, nonessential amino acid and penicillin/streptomycin were added. The cell suspension was put into a culture container and cultured at 37° C. and the $CO_2$ concentration of 5%. The primary isolated porcine alveolar macrophage was total $2\times10^8$ cells/ml and stored at −80° C. The shape of the cultured porcine alveolar macrophage is shown in FIG. 1.

1.2 Isolation of PRRSV and Confirmation of PAM Infection with PRRSV

For virus used in this experiment, a porcine reproductive and respiratory syndrome virus (hereinafter, PRRSV) which was isolated from an infected pig exhibiting abnormal symptoms among JW farm's pigs was used. Tissues of blood, lung, lymph and tonsil from a pig suspected of being infected were pulverized and suspended in the phosphate buffer solution, and the experiment was conducted to isolate virus from samples that were determined as being virus-positive according to PCR Assay.

The PAM isolated in Example 1.1 was divided into $2\times10^6$ cells/ml in a T-25 flask, and upon confirmation of cell adhesion, samples such as sample blood, lung, lymph, tonsil, etc. which were determined as being positive according to the PCR Assay were inoculated with 10 to 100 μl of virus, respectively. After then, when cytopathic effect (CPE) appeared, the samples were collected and stored at −80° C. The T25 flask in which the PAM cells existed was each inoculated with 100 μl of the collected virus, and the virus was confirmed according to the indirect immunofluorescence assay (IFA), and the blind passage culture was continuously performed. More specifically, a cell which was confirmed to be infected with PRRSV was fixed for 5 minutes using 4% paraformaldehyde, and then cleaned three times for 10 minutes by using a buffer solution. After then, it was treated in a 2% BSA solution for 1 hour in order to prevent a non-specific bond of an antibody, and then cleaned three times for 5 minutes. As a primary antibody, mouse anti-PRRSV Mab 4A5 (JBT Cat#9041) was used, and as a secondary antibody, goat anti-mouse IgG FITC (Santacruz) was used.

Figure 2:
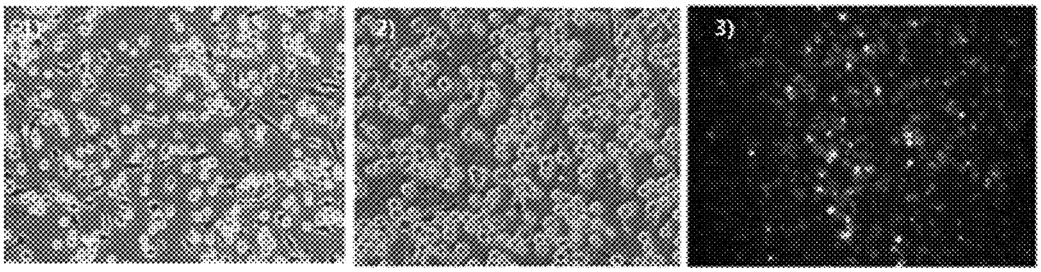
FIG. 2 is a diagram showing the results of determination on the infection with virus by the indirect immuno fluorescence assay after inoculation of a porcine alveolar macrophage with a porcine reproductive and respiratory syndrome virus (hereinafter, PRRSV).

The result is shown in FIG. 2.

As shown in FIG. 2, after 96 hours from the inoculation of the isolated PAM with virus, fluorescence could be confirmed in the PAM cell. From this, it was confirmed that the PAM cell was effectively infected with PRRSV.

1.3 Isolation of Virus Clone According to the Plaque Separation Method

The PAM cell was inoculated in a 6-well plate at a concentration of $3\times10^5$ cells/well, and after 12 hours, the isolated PRRSV was diluted starting from MOI=1 up to 10 times and each of the wells was inoculated with the PRRSV. After culturing it for 1 hour, the medium was removed, and the cell layer infected with virus is covered by a DMEM medium in which 0.5% agarose and 10% fetal bovine serum were contained and cultured at 37° C., 5% and $CO_2$. After about 72 hours, the formation of plaques was confirmed with the naked eye, and each of the plaques was independently separated and purified to isolate a PRRSV clone.

EXAMPLE 2

Isolation of JW-PRRSV (KCTC 12096BP) Through PRRSV Gene Analysis 2.1 Amplification of PRRSV Gene The phylogenetic analysis was performed from gene information of the ORF5 portion of the isolated PRRSV to classify the virus. Genome RNA of the PRRSV was extracted from PRRSV culture medium 150 μl using Viral RNA Extraction kit (Intron. Korea), following the manufacturer instructions. RT-PCR was performed in order to synthesize viral cDNA corresponding to the respective gene segments. 2 μl of 10 pmol ORF5 reverse primer was put into 10 μl of the extracted RNA, and heated at 80° C. for 3 minutes, and then cooled, and RNA inhibitor (Promega, U.S.A) 1 μl, 5×RT buffer solution (50 mM Tris-HCl (Ph 8.3), 75 mM KCL, 3 mM $MgCl_2$, 10 mM DTT), 10 mM dNTP (Promega, U.S.A) 2 μl, and M-MLV reverse transcriptase (Promega, U.S.A) 1 μl were put and amplified at 37° C. for 1 hour and 30 minutes. PCR was performed using the synthesized cDNA as a template. PCR was repeated 34 times, with a cycle of a series of reactions consisting of putting sterile distilled water 16 μl, cDNA 2 μl, and primer 1 μl in a premix tube (Intron) at 94° C. for 5 minutes, degeneration at 94° C. for 20 seconds, annealing at 60° C. for 30 seconds, and stretching at 72° C. for 45 seconds, and lastly, it was cultured at 72° C. for 5 minutes. For the primer used in the experiment, VR2332 (US strain, Genbank accession number, U87383) whose base sequence was reported for base sequence analysis of ORF5 gene, was referred to, and a forward primer (CCA TTC TGT TGG CAA TTT GA (SEQ ID NO:5)) and a reverse primer (CAC CTT TAG GGC ATA TAT CAT (SEQ ID NO:6)) were used.

2.2 Phylogenetic Analysis of Isolated PRRSV

The PCR product was subject to electrophoresis in 1% agarose gel, and then was purely separated as a gel extraction kit (Macherey-Nagel, Germany), and these PCR products were connected to a multicloning site of lac Z gene of a pGEM-T plasmid vector, and each of the genes was subjected to cloning using *E. coli* DH5α competent cell as a host cell. More specifically, *E. coli* DH5α being stored at −70° C. was melt in ice, and then injected by 50-70 μl into a tube in which the connected plasmid DNA was present. After leaving it in ice for 20 minutes, a heat shock was applied at 42° C. for 90 seconds, and then it was left in ice for 3 minutes again. LB (Luria-Bertani) medium 1 ml was put into the tube and cultured in a culture medium at 37° C. for 1 hour, and then uniformly divided in a LB agar medium in which ampicillin (300 mg/ml), X-gal, IPTG, etc. were contained, and cultured at 37° C. for one night. After culturing, white colony was selected and used for plasmid DNA extraction for base sequence analysis. Each of the selected white colonies was put into a LB agar plate 5 ml in which ampicillin was contained, and cultured in a culture medium at 37° C. for one night, and then centrifuged at 3000 rpm for 10 minutes. After centrifugation, plasmid DNA was extracted using QIAprep Spin Miniprep kit (Qiagen, U.S.A.). The gene information of the purified plasmid DNA was analyzed with Workbench Version 4 (CLC Bio, Arthus, Denmark) software, and the phylogenetic analysis diagram was prepared, and the genetic variation was analyzed by comparing nucleotide sequences of original virus species and the passage cultured sequence.

Figure 3:
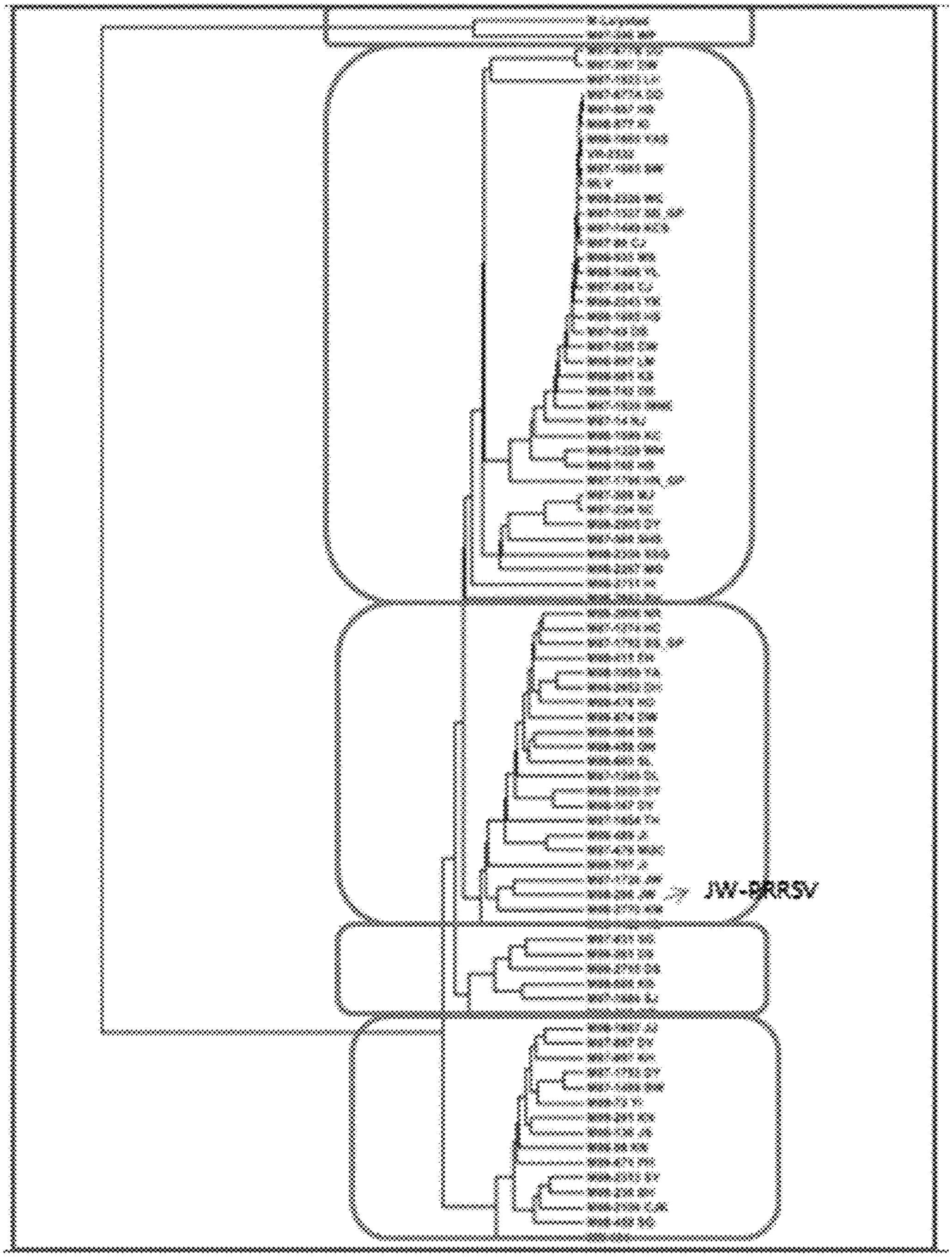
FIG. 3 is a phylogenetic analysis diagram using the analysis results of base sequences of ORF5 of Korean-type PRRSV (JW-PRRSV).
Figure 4:
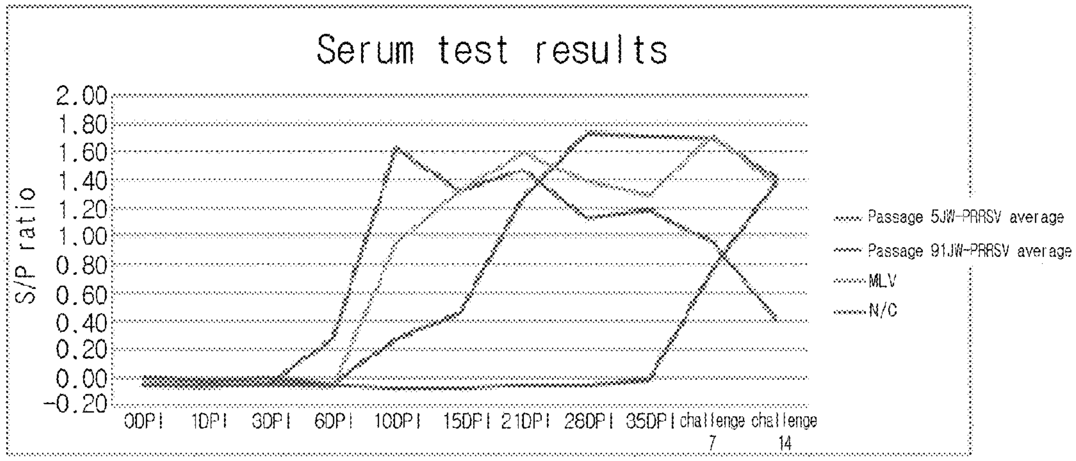
FIG. 4 is a diagram showing the results of measuring the antibody titer after inoculation with isolated Korean-type PRRSV (JW-PRRSV) (passages 5, passages 91).

The result is shown in FIG. 3.

As shown in FIG. 3, it was confirmed that the isolated PRRSB is a novel Korean-type PRRSV which is different from North America type PRRSV in 18% of nucleotides. The novel Korean-type PRRSV was named as JW-PRRSV, and deposited with Number KCTC 12096BP on Dec. 2, 2011.

EXAMPLE 3

Confirmation of Immunogenicity of a Vaccine Developed Using the Korean-Type PRRSV (Hereinafter, JW-PRRSV) (Passages 5, Passages 91)

3.1 Clinical Measurements after Inoculation with JW-PRRSV

In order to develop the newly isolated JW-PRRSV as a vaccine, pigs were inoculated with JW-PRRSV of passages 5 and passages 91, and then the effect was observed. More specifically, 12 colostrum-derived pigs that showed PRRSV-negative and were SPF (Specific-Pathogen-Free) were grouped into total four groups: Passages 5 JW-PRRSV, Passages 91 JW-PRRSV, MLV vaccine (commercial vaccine), and negative control, to confirm immunogenicity (Table 1).

TABLE 1

| CD-pig Entity Number | Contents |
|---|---|
| B09-011<br>B09-012<br>B09-013 | Group inoculated with 2 ml of Passages 5 JW-PRRSV |
| H10-002<br>H10-004<br>B09-014 | Group inoculated with 2 ml of Passages 91 JW-PRRSV |
| B09-008<br>B09-009<br>B09-010 | Group inoculated with MLV vaccine |
| H10-005<br>H10-006<br>H10-007 | Negative control |

Each group was inoculated with 2 ml of virus at $1\times10^5$ PFU/ml, and after 1 day, 3 days, 6 days, 10 days, 15 days, 21 days, 28 days and 35 days from the inoculation, clinical symptoms such as body temperature/motility/food intake, etc. were observed. After 37 days from the inoculation, the pigs were challenged with original virulent JW field-virus at $1\times10^4$ PFU/ml and monitored for the same items. More specifically, body temperature and motility were measured on the same time twice a day during the experimental period, and the motility was monitored in such a manner that scores were given from 0 score to 4 scores at an interval of 0.5 score through the observation for the entities (0 score: no motility, 1 score: weak motility, 2 scores: normal motility, 3 scores: good motility, 4 scores: very good motility). In addition, for food intake, the restricted feeding was performed according to weight, and when intake all amount within 10 minutes, the food intake was determined as very good (4 scores), and according to the time taken for intake all amount the feeds, scores were given from 0 score to 4 scores at an interval of 0.5 score. The overall motility and the food intake were evaluated by the sum of the scores obtained as above.

The result is shown in Table 2.

TABLE 2

| Experimental group | Motility Food intake |
|---|---|
| Group inoculated with Passages 5 JW-PRRSV | The group was managed with good food intake and motility until the experiment was terminated. |
| Group inoculated with Passages 91 JW-PRRSV | The group was managed with good food intake and motility until the experiment was terminated. |
| Group inoculated with MLV vaccine | The group was managed with good food intake and motility until the experiment was terminated. |
| Control | The day of challenge: After 10 to 15 minutes from inoculation, H10-005 entity vomited and showed reduced feed intake.<br>H10-006 entity showed reduced motility (when feeding after inoculation, the pig was not willing to intake the feed, but the pig took all amount of the feed)<br>1 day after challenge: Good food intake and motility. After 15 hours from inoculation, the body temperature increased by 1.6 degree as compared to the date of challenge. After 24 hours from inoculation, the body temperature increased by 0.96<br>2 days after challenge: Good food intake and motility. |

As shown in Table 2, as the result of the interpretation of the scores, the Groups inoculated with Passages 5 JW-PRRSV, Passages 91 JW-PRRSV and MLV vaccine showed good food intake and motility until the experiment was terminated. Therefore, it was confirmed that both Passages 5 JW-PRRSV and Passages 91 JW-PRRSV lead to the virus protection equivalent to the commercial MLV vaccine.

3.2 Measurement of the Antibody Titer after Inoculation with Korean-Type PRRSV (JW-PRRSV)

In order to evaluate the vaccine effect of JW-PRRSV, virus was inoculated under the same conditions as in Example 3.1 and then the antibody titer was measured. After 37 days from inoculation, the pigs were challenged with original virulent JW field-virus at $1\times10^4$ PFU/ml and monitored for the same items as in Example 3.1. After 14 days from challenge, an autopsy was conducted for all entities, and quantitative PCR was performed for lung, lymph, tonsil, lien, liver, encephalon, and kidney. In order to enable a vaccine virus to lead to the protection against a field-virus, primarily, an antibody should be determined as being positive in the serum test, and the virus should have the virus neutralizing ability. Whether the antibody titer in the inoculated animal was converted into positive was measured by the ELISA (HerdChek: PRRS 2XR ELISA kit (IDEXX laboratories, Westbrook, Me., USA)) method. The presence or absence of PRRSV antibody was expressed with S/P ratio, and when the S/P ratio was 0.4 or higher, it was determined as being positive.

The result is shown in Tables 3 and 4.

As shown in Tables 3 and 4, it could be confirmed that after 10 days from the inoculation, in the experimental groups inoculated with Passages 5 JW-PRRSV, Passages 91 JW-PRRSV and MLV vaccine, except for control, an increase in antibody titer was expressed, and on 35 days after inoculation, in all experimental groups, the antibody titer was converted into positive.

3.3 Measurement of Virus Titers by JW-PRRSV

In order to evaluate the vaccine effect of JW-PRRSV, the groups were inoculated with virus under the same conditions as in Example 3.1, and then PRRSV virus titers in blood and tissues after autopsy were measured. After 37 days from inoculation, the pigs were challenged with original virulent JW field-virus at $1\times10^4$ PFU/ml and monitored for the same items as in Example 3.1.

TABLE 3

| | PRRS S/R ratio | | | | | | | | | | |
|---|---|---|---|---|---|---|---|---|---|---|---|
| Entity | 0 DPI 3/16 | 1 DPI 3/17 | 3 DPI 3/19 | 6 DPI 3/22 | 10 DPI 3/26 | 15 DPI 3/31 | 21 DPI 4/6 | 28 DPI 4/13 | 35 4/20 | challenge 7 4/29 | challenge 14 5/6 |
| B09-011 | −0.02 | −0.01 | −0.02 | 0.43 | 2.39 | 2.46 | 2.87 | 2.27 | 2.37 | 1.63 | 1.05 |
| B09-012 | −0.07 | −0.09 | −0.05 | 0.25 | 0.88 | 0.20 | 0.33 | 0.35 | 0.51 | 0.55 | 0.06 |
| B09-013 | −0.07 | −0.09 | −0.05 | 0.14 | 1.59 | 1.32 | 1.23 | 0.79 | 0.67 | 0.69 | 0.13 |
| Passage 5 JW-PRRSV | −0.05 | −0.06 | −0.04 | 0.27 | 1.62 | 1.33 | 1.48 | 1.14 | 1.18 | 0.96 | 0.41 |
| H10-002 | 0.01 | −0.03 | 0.00 | 0.00 | 0.05 | 0.27 | 2.34 | 2.82 | 2.29 | 2.17 | 1.86 |
| H10-004 | 0.00 | −0.02 | −0.02 | −0.07 | 0.09 | 0.66 | 0.99 | 1.72 | 1.16 | 2.27 | 0.62 |
| B09-014 | −0.01 | −0.02 | −0.01 | −0.06 | 0.67 | 0.44 | 0.51 | 0.66 | 0.70 | 0.65 | 1.78 |
| Passage 91 JW-PRRSV | 0.00 | −0.02 | −0.01 | −0.04 | 0.27 | 0.46 | 1.28 | 1.73 | 1.72 | 1.70 | 1.42 |
| B09-008 | 0.02 | −0.02 | −0.04 | −0.07 | 0.75 | 1.52 | 1.72 | 1.50 | 1.56 | 2.14 | 1.76 |
| B09-009 | −0.06 | −0.09 | −0.07 | −0.09 | 1.02 | 1.34 | 1.52 | 1.39 | 1.35 | 2.04 | 1.59 |
| B09-010 | −0.04 | −0.04 | −0.06 | −0.05 | 1.10 | 1.13 | 1.55 | 1.28 | 1.00 | 0.97 | 0.78 |
| MLV | −0.03 | −0.05 | −0.06 | −0.07 | 0.96 | 1.33 | 1.60 | 1.39 | 1.30 | 1.72 | 1.38 |
| H10-005 | −0.02 | −0.04 | −0.02 | −0.04 | −0.08 | −0.07 | −0.08 | −0.06 | −0.03 | 0.43 | 1.43 |
| H10-006 | −0.03 | −0.03 | −0.04 | −0.05 | −0.06 | −0.09 | −0.03 | −0.04 | 0.00 | 1.03 | 1.47 |
| H10-007 | −0.11 | −0.09 | −0.08 | −0.07 | −0.10 | −0.07 | −0.06 | −0.05 | −0.02 | 0.86 | 1.27 |
| N/C Average | 0.05 | −0.05 | −0.05 | −0.05 | −0.08 | −0.08 | −0.06 | −0.03 | −0.02 | 0.77 | 1.39 |

The result is shown in Table 4.

TABLE 4

| Inoculated virus | Entity | NA ORF7 Log TCID 50/ml | | | | | | | | |
|---|---|---|---|---|---|---|---|---|---|---|
| | | 0 DPI | 1 DPI | 3 DPI | 6 DPI | 10 DPI | 15 DPI | 21 DPI | 35 DPI | Challenge 7 DPI |
| P9 | B09-011 | N.D. | 2.627 | 2.812 | 3.265 | N.D. | N.D. | N.D. | N.D. | N.D. |
| | B09-012 | N.D. | 2.762 | 3.333 | 3.417 | 1.394 | N.D. | N.D. | N.D. | N.D. |
| | B09-013 | N.D. | 2.414 | 3.166 | 2.338 | N.D. | N.D. | N.D. | N.D. | N.D. |
| P91 | B09-014 | N.D. | N.D. | N.D. | N.D. | N.D. | N.D. | N.D. | N.D. | N.D. |
| | H10-002 | N.D. | N.D. | N.D. | N.D. | N.D. | N.D. | N.D. | N.D. | N.D. |
| | H10-004 | N.D. | N.D. | N.D. | N.D. | N.D. | N.D. | N.D. | N.D. | N.D. |
| MLV | B09-008 | N.D. | N.D. | N.D. | 0.612 | 0.412 | N.D. | N.D. | N.D. | N.D. |
| | B09-009 | N.D. | N.D. | N.D. | 0.677 | N.D. | N.D. | N.D. | N.D. | N.D. |
| | B09-010 | N.D. | N.D. | N.D. | 0.606 | N.D. | N.D. | N.D. | N.D. | N.D. |
| N/C | H10-009 | N.D. | N.D. | N.D. | N.D. | N.D. | N.D. | N.D. | N.D. | 2.794 |
| | H10-008 | N.D. | N.D. | N.D. | N.D. | N.D. | N.D. | N.D. | N.D. | 3.213 |
| | H10-007 | N.D. | N.D. | N.D. | N.D. | N.D. | N.D. | N.D. | N.D. | 3.22 |

As shown in Table 4, in the group inoculated with Passages 5 JW-PRRSV, there was an entity in which virus was detected in blood until 10 days from the inoculation, and in the group inoculated with Passages 91 JW-PRRSV, no virus was detected in blood both before and after the inoculation. In the group inoculated with commercial live vaccine MLV, a few of virus was detected on 6 days after the inoculation, and no virus was detected after challenge. In the negative control, a considerable amount of virus was detected in blood on 7 days after challenge.

EXAMPLE 4

Confirmation of Safety and Immunogenicity of a Vaccine Developed Using Korean-Type PRRSV (JW-PRRSV)

20 colostrum-derived pigs that showed PRRSV-negative and were SPF (Specific-Pathogen-Free) were grouped into total five groups: MLV vaccine (commercial vaccine; G-A), Passages 3 JW-PRRSV (G-B), Passages 120 JW-PRRSV (G-C), negative control 1 (negative control against challenge; G-D), and negative control 2 (negative control in the entire experiment; G-E). Each group was inoculated with 2 ml of virus at $1\times10^5$ PFU/ml, and after 7 days, 14 days, 21 days, 28 days and 35 days after inoculation, clinical symptoms such as body temperature/motility/food intake, etc. were observed, and the measurement of virus titers in blood and antibody titers, blood cell analysis, and clinical symptom analysis were conducted by gathering blood. And then, after 42 days from inoculation, the pigs were challenged with original virulent JW field-virus at $1\times10^4$ PFU/ml and monitored for the same items. In order to enable a vaccine virus to lead to the protection against a field-virus, primarily, an antibody should be determined as being positive in the serum test, and the virus should have the virus neutralizing ability. Whether the antibody titer in the inoculated animal was converted into positive was measured by the ELISA (HerdChek: PRRS 2XR ELISA kit (IDEXX laboratories, Westbrook, Me., USA)) method, and whether to induce the neutralization antibody tilters was measured using the VN (virus neutralization) test.

4.1 Measurement of Virus Titers According to the RT-PCR Method

In order to measure the amount of PRRSV, a primer (ORF7) was manufactured with reference to VR2332 (US strain, Genebank accession number, U87382) whose base sequence was already reported (forward primer, ATG ATG RGC TGG CAT TCT (SEQ ID NO:1), reverse primer ACA CGG TCG CCC TAA TTG (SEQ ID NO:2)). Genome RNA of the PRRSV was extracted from PRRSV culture medium 150 μl using Viral RNA Extraction kit (Intron. Korea), following the kit's manufacturer instructions, and RT-PCR was performed in order to synthesize viral cDNA corresponding to the respective gene segments. 2 μl of 10 pmol ORF5 reverse primer was put into 10 μl of the extracted RNA, and heated at 0° C. for 3 minutes, and then cooled, and RNA inhibitor (Promega, U.S.A) 1 μl, 5×RT buffer solution (50 mM Tris-HCl (Ph 8.3), 75 mM KCL, 3 mM $MgCl_2$, 10 mM DTT), 10 mM dNTP (Promega, U.S.A) 2 μl, and M-MLV reverse transcriptase (Promega, U.S.A) 1 μl were put and amplified at 37° C. for 1 hour and 30 minutes. PCR was repeated 40 times, with a cycle of a series of reactions consisting of using synthesized cDNA 2 μl, Sybr green dye 10 ul (Bio-Rad Korea), sterile distilled water 6 μl, primer 1 μl at 95° C. for 3 minutes, degeneration at 95° C. for 20 seconds, annealing at 60° C. for 20 seconds, and stretching at 72° C. for 30 seconds, and the reaction at 55° C. for 1 minute and 60° C. for 10 seconds was repeated 71 times and then closed. Since RT-PCR produced a PCR reaction with DNA whose continuous diluted amount was known, basically, in the region where the amplification occurs exponentially, calibration curve was prepared with threshold cycle (Ct value) which may be a constant amplified product amount on a horizontal axis and an initial DNA amount on a vertical axis, and the unknown concentration of samples was also reacted under the same conditions to calculate Ct values to measure target DNA amounts.

The result is shown in Table 5.

TABLE 5

| Classification | | Immunization DPI-0 | DPI-7 | DPI-14 | DPI-21 | DPI-28 | DPI-35 | Challenge DPI-0 | DPI-7 | DPI-14 | DPI-21 | DPI-28 | DPI-35 | DPI-42 |
|---|---|---|---|---|---|---|---|---|---|---|---|---|---|---|
| | | NA ORF7 JW (PRRS-NA TYPE) | | | | | | NA ORF7 JW (PRRS-NA TYPE) | | | | | | |
| MLV | A-1 | N.D. | 1.313 | −1.74 | −0.173 | −0.273 | −0.161 | −1.681 | 0.27 | −0.633 | −1.285 | N.D. | N.D. | N.D. |
| Inoculation | A-2 | N.D. | 1.852 | 0.537 | 0.536 | −0.241 | 0.112 | N.D. | −0.281 | N.D. | N.D. | N.D. | N.D. | N.D. |
| (G-A) | A-3 | N.D. | 1.232 | −1.316 | 0.096 | 0.416 | −0.171 | 0.441 | 1.804 | N.D. | N.D. | N.D. | N.D. | N.D. |
| | A-4 | N.D. | 1.915 | 0.982 | 1.303 | 1.529 | 1.365 | 0.651 | 0.722 | N.D. | −0.312 | −0.128 | N.D. | N.D. |
| P-3 | B-1 | N.D. | 3.795 | 2.459 | 0.095 | 0.016 | −1.713 | N.D. | N.D. | N.D. | N.D. | N.D. | N.D. | N.D. |
| Inoculation | B-2 | N.D. | 3.747 | 3.412 | 2.121 | 0.762 | −0.665 | N.D. | N.D. | N.D. | −0.761 | −0.774 | −0.774 | N.D. |
| (G-B) | B-3 | N.D. | 3.228 | 0.824 | 0.826 | 0.151 | −0.659 | N.D. | N.D. | N.D. | N.D. | N.D. | N.D. | N.D. |
| | B-4 | N.D. | 2.609 | 3.155 | 1.932 | 2.754 | 0.121 | N.D. | N.D. | N.D. | −0.283 | N.D. | N.D. | N.D. |
| P-120 | C-1 | N.D. | −0.318 | 0.975 | 0.110 | N.D. | −0.168 | N.D. | N.D. | N.D. | N.D. | N.D. | N.D. | N.D. |
| Inoculation | C-2 | N.D. | −0.779 | −1.033 | −0.901 | −1.174 | −0.039 | N.D. | 0.11 | N.D. | 0.077 | −1.456 | N.D. | N.D. |
| (G-C) | C-3 | N.D. | N.D. | 1.156 | 0.887 | −1.459 | −0.787 | N.D. | 2.301 | 0.111 | N.D. | −0.774 | N.D. | N.D. |
| | C-4 | N.D. | 0.025 | N.D. | 0.550 | −1.064 | −0.443 | N.D. | 0.183 | N.D. | N.D. | N.D. | N.D. | N.D. |
| P/C | D-1 | N.D. | −0.662 | N.D. | −0.273 | N.D. | −2.398 | N.D. | 2.567 | N.D. | N.D. | −1.687 | N.D. | N.D. |
| (G-D) | D-2 | N.D. | −1.356 | N.D. | N.D. | −1.004 | −0.82 | N.D. | 2.032 | −2/22 (Tue) Dead | | | | |
| | D-3 | N.D. | −1.672 | N.D. | N.D. | −1.045 | −2.064 | N.D. | 0.263 | 0.349 | 0.164 | N.D. | N.D. | N.D. |
| | D-4 | N.D. | −1.173 | −0.288 | N.D. | N.D. | −0.881 | N.D. | 0.048 | 0.619 | 0.345 | N.D. | N.D. | N.D. |
| N/C | E-1 | N.D. | −0.468 | N.D. | −0.311 | N.D. | −0.438 | N.D. | N.D. | N.D. | −1.240 | N.D. | N.D. | N.D. |
| (G-E) | E-2 | N.D. | −0.192 | N.D. | −0.278 | −0.337 | −0.341 | N.D. | N.D. | N.D. | N.D. | N.D. | N.D. | N.D. |
| | E-3 | N.D. | −0.376 | N.D. | N.D. | −1.215 | −0.07 | N.D. | N.D. | N.D. | N.D. | N.D. | N.D. | N.D. |
| | E-4 | N.D. | N.D. | N.D. | N.D. | N.D. | N.D. | N.D. | N.D. | N.D. | N.D. | N.D. | N.D. | N.D. |

As shown in Table 5, in the group inoculated with MLV vaccine (G-A), after 7 days from inoculation, in all entities, virus was detected, and there was an entity in which virus was detected until 35 days. In the group inoculated with Passages 5 JW-PRRV (G-B), after 7 days from inoculation, in all entities, virus having a high tilter was detected, and virus was continuously detected until 28 days, and there was an entity in which virus was detected until 35 days. In the group inoculated with Passages 120 JW-PRRV (G-C), after 14 days from inoculation, in two entities, virus was detected, and virus was remained until 21 days after inoculation, and no virus was detected from 28 days. From this result, it can be known that this vaccine showed virus tilters 6 times lower than commercial MLV vaccine (G-A) and the residence day in blood was also short. In addition, in the group inoculated with MLV vaccine (G-A), in all entities, virus was detected, but in the group inoculated with Passages 120 JW-PRRV (G-C), only in two entities, virus was detected. After 42 days from challenge, in the group inoculated with MLV vaccine (G-A), after 7 days from inoculation, in three entities, virus in blood was detected, and in the group inoculated with Passages 5 JW-PRRV (G-B), in all four entities, no virus was detected. This is deemed to be homologous challenge protection (Report: Colloquium on Prospects for Development of an Effective PRRS Virus Vaccine, Aug. 13, 2007—D. L. Rock, PhD, University of Illinois). In the group inoculated with Passages 120 JW-PRRV (G-C), after 7 days from challenge, in two entities, virus was detected. In the negative group (G-D), after 7 days from challenge, in two entities, a considerable amount of virus was detected in blood, and out of these entities, one entity died after 14 days from inoculation. An autopsy was conducted on this entity, and the virus tilters for lung, lymph, tonsil, kidney, bronchus, liver, etc. were measured.

The result is shown in Table 6.

TABLE 6

| Measurement of virus tilters in tissues for G-D entity-2 | |
|---|---|
| Autopsy Blood | Negative (Log $TCID_{50}$/ml) |
| lung | 2.767 |
| liver | −0.171 |
| kidney | −0.366 |
| bronchus | 0.681 |
| lymph | 0.107 |
| tonsil | 2.685 |

As shown in Table 6, it could be confirmed that in the lung and tonsil of the died negative control, a considerable amount of virus was detected.

4.2 Measurement Result of Antibody Titers in Blood

The blood samples obtained from each of the inoculated groups were measured by the ELISA (HerdChek: PRRS 2XR ELISA kit (IDEXX laboratories, Westbrook, Me., USA) method to measure the antibody titers in blood against PRRSV. The presence or absence of the formation of the antibody against PRRSV was expressed with S/P ratio, and when the S/P ratio is 0.4 or higher, it was determined as positive.

Figure 5:
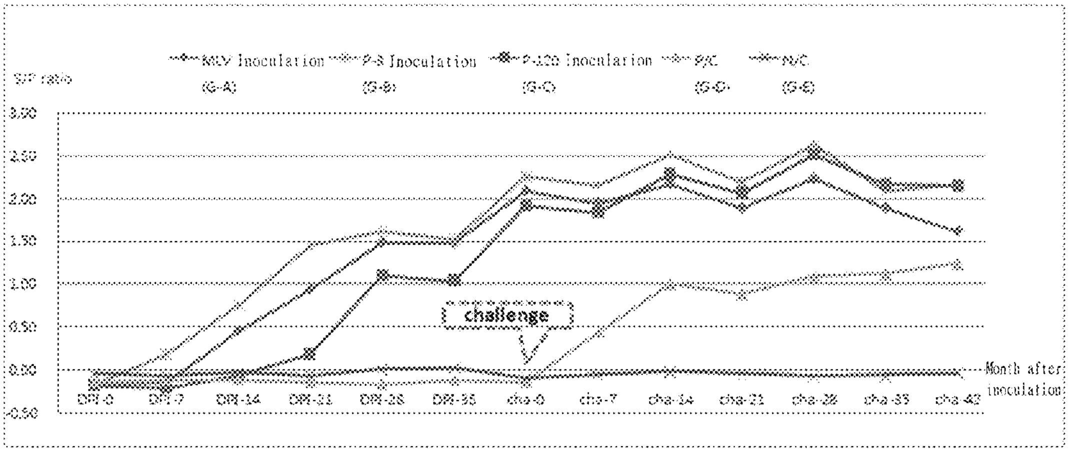
FIG. 5 is a diagram showing the results of measuring the antibody titer in blood after inoculation with Korean-type PRRSV (JW-PRRSV) (passages 3, passages 120).

The result is shown in Table 7 and FIG. 5.

TABLE 7

| | | Immunization | | | | | | Challenge | | | | | | |
|---|---|---|---|---|---|---|---|---|---|---|---|---|---|---|
| Classification | | DIP-0 | DPI-7 | DPI-14 | DPI-21 | DPI-28 | DPI-35 | cha-0 | cha-7 | cha-14 | cha-21 | cha-28 | cha-35 | cha-42 |
| MLV | A-1 | −0.18 | −0.11 | 0.75 | 1.50 | 1.72 | 1.63 | 2.23 | 2.15 | 2.71 | 2.22 | 2.67 | 2.21 | 1.96 |
| Inoculation | A-2 | −0.14 | −0.17 | 0.81 | 1.50 | 1.91 | 1.70 | 2.65 | 2.55 | 2.84 | 2.63 | 2.92 | 2.39 | 2.08 |
| (G-A) | A-3 | −0.17 | −0.19 | 0.03 | 0.37 | 1.18 | 1.55 | 2.12 | 1.82 | 1.80 | 1.41 | 1.81 | 1.55 | 1.29 |
| | A-4 | −0.13 | −0.12 | 0.24 | 0.38 | 1.14 | 2.03 | 1.38 | 1.29 | 1.34 | 1.31 | 1.55 | 1.44 | 1.15 |
| Average | | −0.16 | −0.15 | 0.46 | 0.94 | 1.49 | 1.18 | 2.10 | 1.05 | 2.18 | 1.89 | 2.24 | 1.90 | 1.62 |
| P-3 | B-1 | −0.17 | 0.01 | 0.75 | 1.39 | 1.69 | 1.68 | 2.47 | 2.30 | 2.61 | 2.46 | 2.86 | 2.31 | 2.38 |
| Inoculation | B-2 | −0.11 | 0.80 | 1.30 | 1.05 | 2.10 | 1.93 | 2.56 | 2.17 | 2.53 | 2.15 | 2.67 | 2.09 | 2.24 |
| (G-B) | B-3 | −0.18 | −0.04 | 0.45 | 0.78 | 0.85 | 1.03 | 2.13 | 2.12 | 2.46 | 2.16 | 2.55 | 1.96 | 2 |
| | B-4 | −0.23 | −0.03 | 0.53 | 1.78 | 1.77 | 1.44 | 1.69 | 2.06 | 2.46 | 2.04 | 2.48 | 2.03 | 2.06 |
| Average | | −0.17 | 0.19 | 0.76 | 1.45 | 1.62 | 1.52 | 2.26 | 2.26 | 2.52 | 2.20 | 2.64 | 1.10 | 1.17 |
| P-120 | C-1 | −0.22 | −0.39 | −0.31 | −0.28 | 1.13 | 1.17 | 2.18 | 2.23 | 2.76 | 2.32 | 2.77 | 2.21 | 2.23 |
| Inoculation | C-2 | −0.16 | −0.13 | 0.12 | 0.51 | 1.06 | 1.00 | 2.02 | 1.87 | 2.04 | 1.94 | 2.37 | 2.12 | 2.06 |
| (G-C) | C-3 | −0.14 | −0.17 | −0.03 | 0.43 | 1.01 | 0.87 | 1.66 | 1.66 | 2.19 | 2.11 | 2.51 | 2.19 | 2.11 |
| | C-4 | −0.20 | −0.14 | −0.04 | 0.07 | 1.19 | 1.12 | 1.63 | 1.60 | 2.15 | 1.91 | 2.4 | 2.18 | 2.2 |
| Average | | −0.18 | −0.21 | −0.07 | 0.18 | 2.10 | 1.04 | 1.92 | 2.64 | 2.28 | 2.07 | 2.51 | 2.18 | 2.15 |
| P/C | D-1 | −0.13 | −0.17 | −0.10 | −0.17 | −0.23 | −0.11 | −0.17 | 0.97 | 2.48 | 2.40 | 2.64 | 2.1 | 2.02 |
| (G-D) | D-2 | −0.05 | −0.02 | −0.09 | −0.07 | −0.09 | −0.11 | −0.09 | 0.48 | | 2/11 (Tue) Dead | | | |
| | D-3 | −0.10 | −0.07 | −0.04 | −0.15 | −0.18 | −0.13 | −0.20 | 0.24 | 0.40 | 0.06 | 0.5 | 0.9 | 0.95 |
| | D-4 | −0.27 | −0.23 | −0.22 | −0.18 | −0.18 | −0.14 | −0.10 | 0.07 | 0.12 | 0.19 | 0.12 | 0.34 | 0.74 |
| Average | | −0.14 | −0.12 | −0.11 | −0.14 | −0.17 | −0.12 | −0.14 | 0.44 | 1.00 | 0.88 | 1.09 | 1.11 | 1.24 |
| N/C | E-1 | −0.06 | −0.11 | −0.13 | −0.10 | −0.02 | −0.09 | −0.15 | −0.07 | −0.09 | −0.04 | −0.08 | −0.06 | −0.1 |
| (G-E) | E-2 | −0.04 | −0.05 | −0.02 | −0.05 | 0.16 | 0.35 | −0.02 | −0.02 | 0.01 | −0.04 | −0.06 | −0.05 | 0 |
| | E-3 | −0.02 | −0.05 | 0.01 | −0.07 | −0.07 | −0.08 | −0.10 | −0.08 | −0.01 | −0.06 | −0.08 | −0.07 | −0.03 |
| | E-4 | −0.03 | −0.06 | 0.01 | −0.04 | −0.05 | −0.10 | −0.10 | −0.06 | 0.00 | −0.05 | −0.04 | −0.06 | −0.02 |
| Average | | −0.04 | −0.07 | −0.03 | −0.07 | 0.01 | 0.02 | −0.09 | −0.08 | −0.02 | −0.05 | −0.07 | −0.06 | −0.04 |

As shown in Table 7 and FIG. 5, in the group inoculated with commercial MLV vaccine (G-A), after 14 days from inoculation, in two entities, virus tilters were converted into positive, and after 25 days, in four entities, virus was converted into positive. In the group inoculated with Passages 5 JW-PRRV (G-B), after 7 days from inoculation, in one entity, virus tilters were converted into positive, and after 14 days, in four entities, virus was converted into positive. In the group inoculated with Passages 120 JW-PRRV (G-C), after 21 days from inoculation, two entities were converted into positive, and after 14 days, in four entities, virus was converted into positive. From the above, it was confirmed that the group inoculated with Passages 120 JW-PRRV (G-C) is a candidate substance which can sufficiently induce antibody tilter while being safety.

4.3 Blood Cell Analysis Result

The values of various blood cells present in blood were measured in the blood samples collected from each of the inoculated groups by using an auto cytometry.

Figure 6:
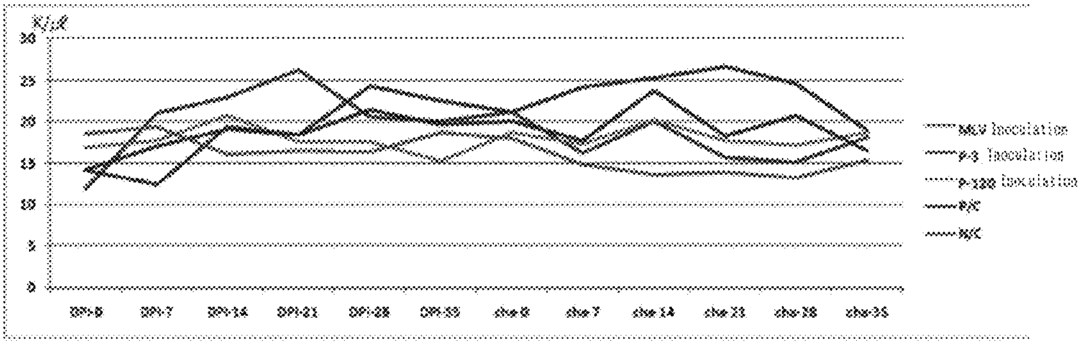
FIG. 6 is a diagram showing the results of measuring leukocyte and lymphocyte values in the blood of entities after inoculation with Korean-type PRRSV (JW-PRRSV) (passages 3, passages 120).
Figure 6:
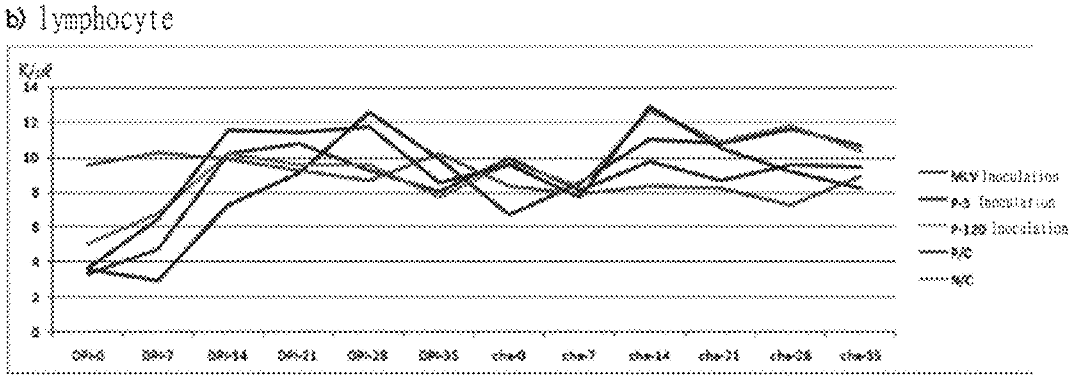

The result is shown in FIG. 6.

As shown in FIG. 6, it could be confirmed that in the group inoculated with Passages 3 JW-PRRV (G-B), white blood cells slightly increased, but in other groups, the change in white blood cell value was not great until the experiment is terminated (a). In addition, as a result of the measurement of a lymphocyte in blood, even after inoculation of the vaccine candidate group, it showed the normal lymphocyte values being 4.3 to 13,600 cells/μl (b). This result shows that the vaccine candidate substance of the present invention is a safe substance that does not lead to inflammation in an entity.

4.4 Clinical Analysis Result

After challenge with a vaccine, clinical symptoms appearing on pigs were observed. Body temperature and motility were measured on the same time twice a day during the experimental period, and for the motility, scores were given from 0 point to 4 scores at an interval of 0.5 score through individual observation (0 score: no motility, 1 score: weak motility, 2 scores: normal motility, 3 scores: good motility, 4 scores: very good motility). For food intake, the restricted feeding was performed according to weight and when intake all amount within 10 minutes, the food intake was determined as very good (4 scores), and according to the time taken for intake all amount the feeds, scores were given from 0 score to 4 scores at an interval of 0.5 score.

Figure 7:
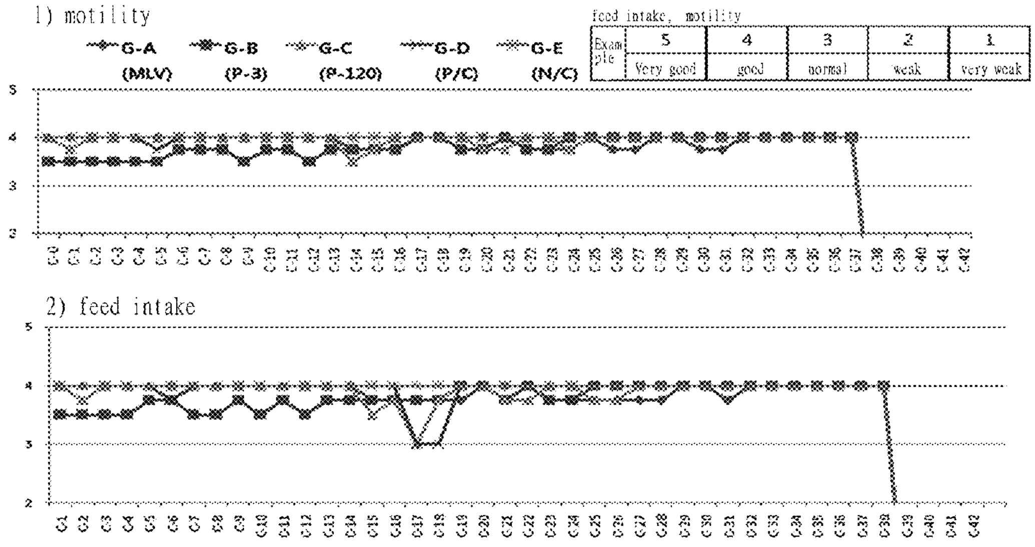
FIG. 7 is a diagram showing the results of analyzing clinical symptoms of entities after inoculation with Korean-type PRRSV (JW-PRRSV) (passages 3, passages 120).

The result is shown in Table 8 and FIG. 7.

TABLE 8

| Classification | 2/08 (Tue)~2/15(Tue) DPI-Q-7 | 2/16 (Wed)~2/22(Tue) | 2/23 (Wed)~3/1(Tue) | 3/2 (Wed)~ |
|---|---|---|---|---|
| G-A (MLV) | (08-296) P3 challenge nasal, muscle, each 2 ml/ after inoculation of the head, no symptoms such as reduced feed intake and motility, were occur | Good feed intake and motility | Good feed intake and motility Improvement to feed intake of A-1 as from normal to good in which separation through cyanoderma of left ear | Good feed intake and motility Separately managed that isolated from A-1 group and good feed intake and motility |
| G-B (P-3) | After challenge, feed intake and motility have no difference from immunization Weak mobility than the front and hind joints, normal feed intake | Good feed intake and motility Good feed intake and motility recovery that gradually favorable from 16 days of B-4 challenge | Good feed intake and motility Good feed intake and normally recovery of motility from 16 days of B-4 challenge | Good feed intake and motility |
| G-C (P-120) | 1 day: slightly reduced than pigs in 3th feed intake and motility 2 days: recovery to feed intake and motility | Good feed intake and motility recovery fourteen days but slightly slow speed of feed intake than current same group that decrease motility and feed intake of C-3 challenge 12 days | Good feed intake and motility Good activity and feed intake of C-3, but slow speed of feed intake | Good feed intake and motility |
| G-D (P/C) | 6 days: slightly reduced than pigs in 2nd feed intake and motility 6 days: recovery to feed intake and motility | 10 days: generate red spots in whole body that is number 2(exudative epidermitis resemble symptoms) 13 days: state of D-2 suddenly poor in afternoon management 14 days: perish D-2(refer to autopsy result and inspection result) | Good feed intake and motility | Good feed intake and motility |
| G-E (N/C) | Good feed intake and motility | Good feed intake and motility | Good feed intake and motility | Good feed intake and motility |

As shown in Table 8 and FIG. 7, it was observed that the group inoculated with Passages 3 JW-PRRSV (G-B) showed weak motility and food intake, but it was confirmed that the food intake and motility were good without particulars.

EXAMPLE 5

Preparation of JW-PRRSV Vaccine 5.1 Passage Method and Preservation

MARC-145 cell was inoculated with PRRS original virulent virus (120 passages) of more than $10^{40}$ $TCID_{50}$/ml which was confirmed in the identification test and the immunogenicity test and cultured at 37° C. for 4-5 days to obtain virus and frozen and dried or frozen and stored at −80° C. Virulent PRRSV was obtained in the same manner as PRRS original virulent virus, and then frozen and dried or frozen and stored at −80° C., and the original virulent virus was not cultured for 3 passages or more, and the virus tilter did not exceed $10^{4.0}$ $TCID_{50}$/ml 5.2 Bulk Production and Virus Content Test MARC-145 or PAM cells cultured using 850 $cm^2$ roller bottle culture in a medium for cell proliferation and then cultured for passage at an interval of 3 to 5 days. When a single layer of the 850 $cm^2$ roller bottle cultured-cells was formed, the medium for cell proliferation was removed, and it was inoculated with an amount such that the cells were substantially covered and adsorbed at 37° C. for 1 hour. It was rotated and cultured at 37° C. for 4-5 days by removing the inoculation liquid and adding a medium for cell proliferation. The centrifuged virus culture medium was diluted decimal and inoculated in 96 well plate where MARC-145 or PAM cell was cultured and cultured at 37° C. for 7 days, and the cytopathic effect (CPE) was observed. When 80-90% of CPE was expressed after virus culturing, it was aseptically collected and frozen and stored at −80° C.

5.3 Preparation of Test Vaccine

* A test vaccine including isolated virus as an antigen was prepared by adding a protective agent. The three types of test vaccines were prepared by applying a sterile phosphate buffer solution and using a freezer and dryer (production number: 60 PRRS 01, 60 PRRS 02, 60 PRRS 03). The contents of the prepared test vaccines are the same as shown in Table 9, Table 10 and Table 11.

TABLE 9

| 60 PRRS 01 | | |
|---|---|---|
| Raw drug | Contents | Bulk amount |
| PRRS | $10^{6.5}TCID_{50}$/ml | 600 ml |
| TPGG | | 150 ml |
| Total | | 750 ml |

TABLE 10

| 60 PRRS 02 | | |
|---|---|---|
| Raw drug | Contents | Bulk amount |
| PRRS | $10^{6.6}TCID_{50}$/ml | 620 ml |
| TPGG | | 156 ml |
| Total | | 776 ml |

TABLE 11

| 60 PRRS 03 | | |
|---|---|---|
| Raw drug | Contents | Bulk amount |
| PRRS | $10^{6.4}TCID_{50}$/ml | 640 ml |
| TPGG | | 160 ml |
| Total | | 800 ml |

As TPGG (trehalose), not conventionally used LPGG (lactose), was used as a protective agent, pollution which may be generated when preparing a live vaccine due to existing protective agents could be minimized and the safety of the vaccine was increased. The comparison table for the virus content for protective agents is shown in Table 12.

TABLE 12

| Raw drug | Virus Contents | Content after freezing and drying |
|---|---|---|
| PRRS | $10^{6.5}TCID_{50}$/ml | |
| TPGG | | $10^{5.8}TCID_{50}$/ml |
| Total | | $10^{5.8}TCID_{50}$/ml |

5.4 Safety Test of Test Vaccine

In order to test the safety for the test vaccine prepared in Example 5.3, characteristics, vacuum level, hydrogen-ion concentration, containing humidity, aspetic test, mycoplasma irregular test, aberrant virus test, content test, and tilter test were performed at the time of preparation, after 3 months from the preparation, after 6 months from the preparation.

The result of the safety test is shown in Table 13.

TABLE 13

| | | Test results | | | | | | | | |
|---|---|---|---|---|---|---|---|---|---|---|
| | | At the time of preparation | | | After 3 months | | | After 6 months | | |
| Classification | Standard | 01 | 02 | 03 | 01 | 02 | 03 | 01 | 02 | 03 |
| characteristic test | Phase uniform | suitable | suitable | suitable | suitable | suitable | suitable | suitable | suitable | suitable |
| vacuum level | there is transfer | suitable | suitable | suitable | suitable | suitable | suitable | suitable | suitable | suitable |

TABLE 13-continued

| Classification | Standard | Test results: At the time of preparation 01 | 02 | 03 | After 3 months 01 | 02 | 03 | After 6 months 01 | 02 | 03 |
|---|---|---|---|---|---|---|---|---|---|---|
| hydrogen-ion concentration test | 6.0-8.0 | 7.15 | 7.05 | 7.20 | 7.13 | 7.10 | 7.17 | 7.14 | 7.17 | 7.15 |
| containing humidity test | 4% or less | 2.60 | 2.62 | 2.70 | 2.61 | 2.60 | 2.63 | 2.62 | 2.63 | 2.62 |
| aspetic test | no micro-bial growth | suitable | suitable | suitable | suitable | suitable | suitable | suitable | suitable | suitable |
| mycoplasma irregular test | PCR negative | — | — | — | — | — | — | — | — | — |
| aberrant virus test | aberrant virus test | suitable | suitable | suitable | suitable | suitable | suitable | suitable | suitable | suitable |
| content test PRRS | more than $10^{5.0}$/head | 5.8 | 5.7 | 5.7 | 5.7 | 5.6 | 5.6 | 5.6 | 5.6 | 5.5 |
| tilter test PRRS | more than 4 times | 32 | 45 | 45 | 45 | 45 | 45 | 32 | 45 | 32 |

As shown in table 13, it was confirmed that the prepared test vaccines 60 PRRS 01, 60 PRRS 02 and 60 PRRS 03 are suitable in the safety test at the time of preparation, after 3 months from the preparation, after 6 months from the preparation. Therefore, it can be understood that the vaccine using JW-PRRSV which is the novel Korean-type PRRSV of the present invention was a suitable vaccine in terms of safety.

EXAMPLE 6

Confirmation of Safety of Test Vaccine

In order to confirm the most important safety in a live vaccine, test animals, mouse, guinea pig and a target animal, pig were inoculated with the test vaccines and the survival rate for 7 days or 21 days were observed. As the inoculated test vaccines, 60 PRRS 01, 60 PRRS 02 and 60 PRRS 03 prepared in Example 5.3 were used, the test animals and the target animals were inoculated with the test vaccines at the time of preparation, after 3 months from the preparation, after 6 months from the preparation, and the survival rate was observed

6.1 Confirmation of Safety of Test Vaccine in Mouse

8 Mouse Having 15-20 g Weight

The result is shown in Table 14.

TABLE 14

| | | Kind | The number of provided animals | The amount of inoculation | Inoculation path | The number of survived animals/ the number of inoculated animals | results (survival rate) |
|---|---|---|---|---|---|---|---|
| At the time of preparation | | ICR | 8 animals | 0.5 ml | the abdominal cavity | 8/8 | 100% |
| | 60 PRRS 02 | ICR | 8 animals | 0.5 ml | the abdominal cavity | 8/8 | 100% |
| | 60 PRRS 03 | ICR | 8 animals | 0.5 ml | the abdominal cavity | 8/8 | 100% |
| After 3 months | 60 PRRS 01 | ICR | 8 animals | 0.5 ml | the abdominal cavity | 8/8 | 100% |
| | 60 PRRS 02 | ICR | 8 animals | 0.5 ml | the abdominal cavity | 8/8 | 100% |
| | 60 PRRS 03 | ICR | 8 animals | 0.5 ml | the abdominal cavity | 8/8 | 100% |
| After 6 months | 60 PRRS 01 | ICR | 8 animals | 0.5 ml | the abdominal cavity | 8/8 | 100% |
| | 60 PRRS 02 | ICR | 8 animals | 0.5 ml | the abdominal cavity | 8/8 | 100% |
| | 60 PRRS 03 | ICR | 8 animals | 0.5 ml | the abdominal cavity | 8/8 | 100% |

As shown in Table 14, all entities inoculated with test vaccines were survival, and thus it was confirmed that this may be a safe vaccine candidate group.

6.2 Confirmation of Safety of Test Vaccine in Guinea Pig 4 guinea pigs weighing 300-350 g provided, and two guinea pigs were inoculated with the test vaccines by an amount of two heads in muscle or subcutaneously, and the other guinea pigs were inoculated with the test vaccines by an amount of two heads into the abdominal cavity (at the time of preparation, after 3 months from the preparation, after 6 months from the preparation), and observed for 7 days.

The result is shown in Table 15

TABLE 15

| | test vaccine | Kind | The number of provided animals | The amount of inoculation | Inoculation path | observation period | result |
|---|---|---|---|---|---|---|---|
| At the time of preparation | 60 PRRS 01 | Hartley | 2 animals<br>2 animals | 2 heads<br>2 heads | muscle<br>the abdominal cavitay | 7 days | normal |
| | 60 PRRS 02 | Hartley | 2 animals<br>2 animals | 2 heads<br>2 heads | subcutaneous<br>the abdominal cavitay | 7 days | normal |
| | 60 PRRS 03 | Hartley | 2 animals<br>2 animals | 2 heads<br>2 heads | muscle<br>the abdominal cavitay | 7 days | normal |
| After 3 months | 60 PRRS 01 | Hartley | 2 animals<br>2 animals | 2 heads<br>2 heads | muscle<br>the abdominal cavitay | 7 days | normal |
| | 60 PRRS 02 | Hartley | 2 animals<br>2 animals | 2 heads<br>2 heads | subcutaneous<br>the abdominal cavitay | 7 days | normal |
| | 60 PRRS 03 | Hartley | 2 animals<br>2 animals | 2 heads<br>2 heads | muscle<br>the abdominal cavitay | 7 days | normal |
| After 6 months | 60 PRRS 01 | Hartley | 2 animals<br>2 animals | 2 heads<br>2 heads | muscle<br>the abdominal cavitay | 7 days | normal |
| | 60 PRRS 02 | Hartley | 2 animals<br>2 animals | 2 heads<br>2 heads | subcutaneous<br>the abdominal cavitay | 7 days | normal |
| | 60 PRRS 03 | Hartley | 2 animals<br>2 animals | 2 heads<br>2 heads | muscle<br>the abdominal cavitay | 7 days | normal |

As shown in Table 15, in the groups inoculated with test vaccines were survival without any abnormal for 7 days, and thus it was confirmed that this may be a safe vaccine candidate group.

6.3 Confirmation of Safety of Test Vaccine in Piglet

In the target animal, piglets, the safety of test vaccine (at the time of preparation, after 3 months from the preparation, after 6 months from the preparation) was confirmed. 18 healthy pigs showing negative to PRRSV antibody and weighing 8-10 (4-6 weeks) were inoculated with 10 heads, and then observed for 21 days.

The result is shown in Table 16.

TABLE 16

| test vaccine | | The number of provided animals | The amount of inoculation | Inoculation path | observation period | result |
|---|---|---|---|---|---|---|
| At the time | 60 PRRS 01 | 2 animals | 10 heads | muscle | 2 animals | normal |
| of preparation | 60 PRRS 02 | 2 animals | 10 heads | muscle | 2 animals | normal |
| | 60 PRRS 03 | 2 animals | 10 heads | muscle | 2 animals | normal |
| After 3 months | 60 PRRS 01 | 2 animals | 10 heads | muscle | 2 animals | normal |
| | 60 PRRS 02 | 2 animals | 10 heads | muscle | 2 animals | normal |
| | 60 PRRS 03 | 2 animals | 10 heads | muscle | 2 animals | normal |
| After 6 months | 60 PRRS 01 | 2 animals | 10 heads | muscle | 2 animals | normal |
| | 60 PRRS 02 | 2 animals | 10 heads | muscle | 2 animals | normal |
| | 60 PRRS 03 | 2 animals | 10 heads | muscle | 2 animals | normal |

As shown in Table 16, in piglets, no hypersensitivity reaction was expressed within 1-2 hours after inoculation, and it was confirmed that during the observation for 21 days, they were all survival without side effect such as suppuration in an inoculated site, necrosis, fever, and diarrhea. Therefore, it can be understood that the test vaccine of the present invention has the safety suitable as a vaccine of porcine PRRSV.

EXAMPLE 7

Confirmation of Safety of Test Vaccine in SPF Piglet

When a target animal was infected with the test vaccine prepared in Example 5 at a high concentration, the virus infection in blood and tissue was confirmed, and when the target animal was inoculated with continuous passages, it was confirmed whether the pathogenicity of virus was recovered to its original wild-type or the pathogenicity. Starting from the primary inoculation of two pigs in SPF state, they were inoculated with 2 ml of attenuated 120 passages JW-PRRSV $2\times10^6$ PFU/ml in muscle and the virus infection in blood, lung after an autopsy, tonsil and lymph were confirmed after 1 day, 3 days and 7 days. The old and weight, virus history and test schedule of the inoculated individual are shown in Table 17 and the result of the virus infection according to the test schedule was shown in Table 18.

TABLE 17

| Classification | Entity | Old (day) | Weight (kg) | Inoculated virus | Test date |
|---|---|---|---|---|---|
| Primary | 100-2 | 145 | 23.4 | P120 6.3 $TCID_{50}$/ml | 2010. 9.1~9.7 |
| | 100-4 | | 26.6 | P120 6.3 $TCID_{50}$/ml | |
| secondary | 100-1 | 164 | 18.7 | Specimen of primary inoculated entity | 2010. 9.20~9.27 |
| | 100-5 | | 17.3 | Specimen of primary inoculated entity | |
| tertiary | H10-009 | 212 | 34.1 | Specimen of secondary inoculated entity | 2010. 10.13~10.21 |
| | H10-011 | | 38.2 | Specimen of secondary inoculated entity | |
| biquadratic | H10-013 | 227 | 36.5 | Specimen of tertiary inoculated entity | 2010. 10.27~11.03 |
| | H10-014 | | 26.1 | Specimen of tertiary inoculated entity | |
| quantic | 104-3 | 127 | 19.8 | Specimen of biquadratic inoculated entity | 2010. 11.25~12.01 |
| | 104-4 | | 16.7 | Specimen of biquadratic inoculated entity | |

TABLE 18

| primary | entity | 0 day | 1 day | 3 day | 7 days (autopsy) | secondary | entity | 0 day | 1 day | 3 day | 7 days (autopsy) | tertiary | entity | 0 day | 1 day | 3 day | 7 days (autopsy) |
|---|---|---|---|---|---|---|---|---|---|---|---|---|---|---|---|---|---|
| blood | entity w-2 | N.D | N.D | N.D | −0.20 | blood | entity-1 | N.D | N.D | −0.99 | N.D | blood | entity-1 | N.D | N.D | N.D | N.D |
| | entity w-4 | N.D | N.D | N.D | 0.000 | | entity-5 | N.D | N.D | −0.89 | N.D | | entity-2 | N.D | N.D | N.D | N.D |
| lymph | entity w-2 | — | — | — | 0.956 | lymph | entity-1 | — | — | — | 1.100 | lymph | entity-1 | — | — | — | −0.27 |
| | entity w-4 | — | — | — | 0.576 | | entity-5 | — | — | — | 0.98 | | entity-2 | — | — | — | −0.13 |
| tonsil | entity w-2 | — | — | — | 0.607 | tonsil | entity-1 | — | — | — | 0.984 | tonsil | entity-1 | — | — | — | 0.316 |
| | entity w-4 | — | — | — | 0.642 | | entity-5 | — | — | — | 1.126 | | entity-2 | — | — | — | 0.374 |
| lung | entity w-2 | — | — | — | 0.509 | lung | entity-1 | — | — | — | 0.84 | lung | entity-1 | — | — | — | N.D |
| | entity w-4 | — | — | — | 0.776 | | entity-5 | — | — | — | 0.72 | | entity-2 | — | — | — | N.D |

| biquadratic | entity | 0 day | 1 day | 3 day | 7 days (autopsy) | quantic | entity | 0 day | 1 day | 3 day | 7 days (autopsy) |
|---|---|---|---|---|---|---|---|---|---|---|---|
| blood | entity-1 | N.D | N.D | −2.25 | N.D | blood | entity-1 | N.D | N.D | N.D | −1.313 |
| | entity-2 | −2.326 | −0.723 | N.D | −1.295 | | entity-2 | N.D | N.D | N.D | N.D |
| lymph | entity-1 | — | — | — | −0.034 | lymph | entity-1 | — | — | — | −0.574 |
| | entity-2 | — | — | — | 0.365 | | entity-2 | — | — | — | −0.116 |
| tonsil | entity-1 | — | — | — | −0.098 | tonsil | entity-1 | — | — | — | 0.115 |
| | entity-2 | — | — | — | −0.069 | | entity-2 | — | — | — | 0.068 |
| lung | entity-1 | — | — | — | −0.609 | lung | entity-1 | — | — | — | N.D |
| | entity-2 | — | — | — | −0.542 | | entity-2 | — | — | — | N.D |

As shown in Table 18, in the first to fifth target animals, as the result of the measurement of virus tilter in the blood and tissue after passage culturing, up to the fifth inoculation, in the blood, no virus was detected.

In the tissue, low virus tilter was shown, and during 5 passages, the amplification or transfer of virus and clinical symptoms were not shown (*N,D; nondetection). In addition, as the result of observation from the inoculation to an autopsy, it was confirmed that they were all survival without side effect such as suppuration in an inoculated site, necrosis, fever, and diarrhea.

EXAMPLE 8

Confirmation of Virus Shedding

Generally, when it is first inoculated with a live vaccine, virus shedding of the vaccine virus can be observed for 3 to 5 weeks. Since the vaccine virus results in no abnormal symptoms, side effects of virus shedding of the live virulent vaccine virus may be problem. The virus shedding time of the vaccine candidate substance of the present invention was confirmed and compared with existing commercial vaccine. The experimental groups were classified into the ground inoculated with MLV vaccine (A), the group inoculated with 5 Passages JW-PRRSV (B), and the group inoculated with 120 Passages JW-PRRSV (C), and after 7 days, 12 days, 15 days, 19 days, 22 days, 26 days, 29 days, 33 days, and 36 days from the inoculation and after 0 day, 7 days, 14 days, 21 days, 29 days, 35 days and 42 days after challenge, the nasal samples were obtained from the entities of each group, and the virus shedding for each group was confirmed by conducting PCR using virus specific primer. For the primer sequence, the sequence shown in Table 19 was used. PCR was performed in the same manner as the existing method, and was confirmed in 1% agarose gel.

TABLE 19

| Primer name | Sequence (5' → 3') | |
|---|---|---|
| Common EU & NAJ230_F | ATGGCCAGCCA GTCAATCA | (SEQ ID NO: 3) |
| Common EU & NAJ068_R | TCGCCCTAATT GAATAGGTGA | (SEQ ID NO: 4) |

Figure 8:
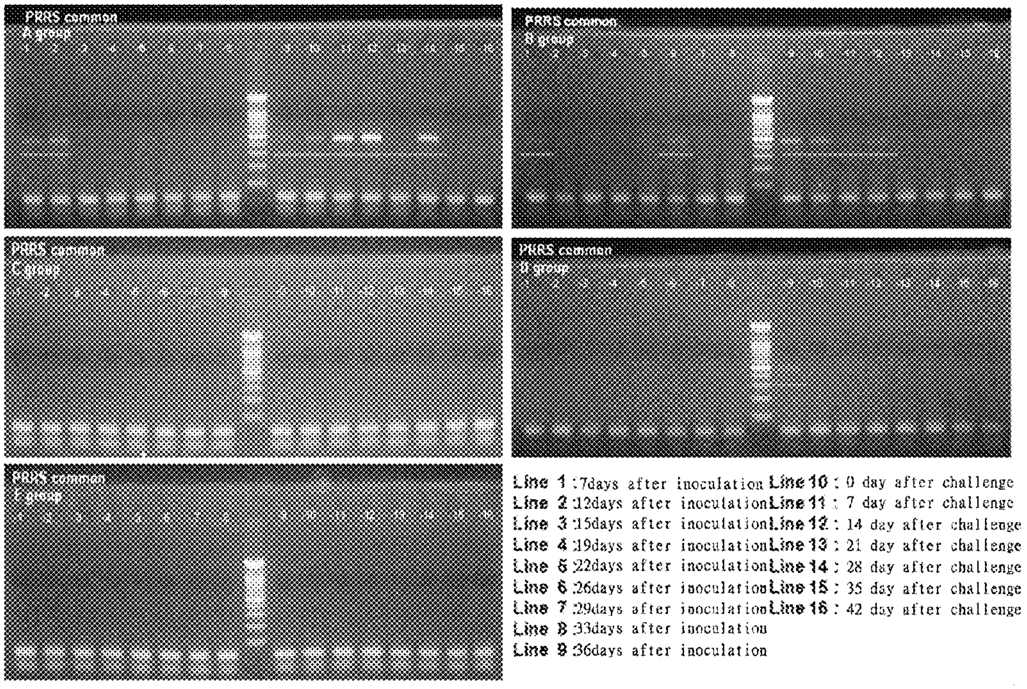
FIG. 8 is a diagram showing the results of confirming virus shedding through PCR after inoculation with Korean-type PRRSV (JW-PRRSV) (passages 3, passages 120) (Group A: Group inoculated with MLV commercial vaccine, Group B: Group inoculated with passages 3 JW-PRRSV, Group C: Group inoculated with passages 120 JW-PRRSV, Group D: positive control, Group E: negative control).

The result is shown in FIG. 8.

As shown in FIG. 8, it was confirmed that in the group inoculated with MLV vaccine (G-A), virus shedding was detected until 12 days from inoculation with the vaccine, and virus shedding was detected until 28 days from challenge. In contrast, in the group inoculated with 120 Passages JW-PRRSV (G-C), virus shedding was not shown during the inoculation period and after infection with field-virus. This means that this vaccine expressed fast virus shedding as compared to the existing commercial vaccine against PRRSV. Long-term virus shedding goes through several reproduction processes, and its toxicity is recovered by a recombinant, so new virus appears and it may be returned to pathogenicity strain. Therefore, the vaccine of the present invention is expected to improve the problem of existing PRRSV vaccine by fast virus shedding.

What is claimed is:

1. A Korean-type porcine reproductive and respiratory syndrome virus (PRRSV) (accession number KCTC 12096BP), wherein the virus is obtained by culturing for 120 passages.

2. A vaccine composition comprising a Korean-type porcine reproductive and respiratory syndrome virus (accession number KCTC 12096BP) as an effective ingredient, wherein the virus is obtained by culturing for 120 passages.

3. The vaccine composition according to claim 2, wherein the vaccine composition further comprises pharmaceutically acceptable adjuvants, excipients or carriers.

4. The vaccine composition according to claim 2, wherein the vaccine composition further comprises a protective agent.

5. The vaccine composition according to claim 4, wherein the protective agent is trehalose.

6. A method for preventing porcine reproductive and respiratory syndrome, comprising administering the virus vaccine composition according to any one of claims 2 and 4 to 5 to pigs.

7. The method according to claim 6, wherein the vaccine composition is inoculated intramuscularly or intranasally.

8. The method according to claim 6, wherein the vaccine composition comprises $2\times10^5$ to $2\times10^7$ PFU/ml of a Korean-type porcine reproductive and respiratory syndrome virus.

9. A diagnosis kit of a Korean-type porcine reproductive and respiratory syndrome virus comprising Korean-type porcine reproductive and respiratory syndrome virus (accession number KCTC 12096BP) or an antigen thereof, wherein the virus is obtained by culturing for 120 passages.

10. A method for detecting Korean-type porcine reproductive and respiratory syndrome virus, comprising detecting a Korean-type porcine reproductive and respiratory syndrome virus (accession number KCTC 12096BP) in a cell to be infected or being infected through an antigen-antibody reaction using Korean-type porcine reproductive and respiratory syndrome virus (accession number KCTC 12096BP) or an antigen thereof.

11. The method according to claim 10, wherein the antigen-antibody reaction analysis is performed using at least one method selected from a group consisting of tissue immunity staining, radio immunoassay (RIA), enzyme immunoassay method (ELISA), Western Blotting, Immunoprecipitation Assay, Immunodiffusion Assay, Complement Fixation Assay, FACS, and protein chip.

* * * * *

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: ORF7-F

<400> SEQUENCE: 1

atgatgrgct ggcattct                                                    18


<210> SEQ ID NO 2
<211> LENGTH: 18
<212> TYPE: DNA
<213> ORGANISM: Artificial Sequence
<220> FEATURE:
<223> OTHER INFORMATION: ORF7-R

<400> SEQUENCE: 2

acacggtcgc cctaattg                                                    18


<210> SEQ ID NO 3
<211> LENGTH: 19
<212> TYPE: DNA
<213> ORGANISM: Artificial Sequence
<220> FEATURE:
<223> OTHER INFORMATION: Common EU&NA J230_F

<400> SEQUENCE: 3

atggccagcc agtcaatca                                                   19
```

-continued

```
<210> SEQ ID NO 4
<211> LENGTH: 21
<212> TYPE: DNA
<213> ORGANISM: Artificial Sequence
<220> FEATURE:
<223> OTHER INFORMATION: Common EU&NA J068_R

<400> SEQUENCE: 4

tcgccctaat tgaataggtg a                                    21


<210> SEQ ID NO 5
<211> LENGTH: 20
<212> TYPE: DNA
<213> ORGANISM: Artificial Sequence
<220> FEATURE:
<223> OTHER INFORMATION: ORF5-F

<400> SEQUENCE: 5

ccattctgtt ggcaatttga                                      20


<210> SEQ ID NO 6
<211> LENGTH: 21
<212> TYPE: DNA
<213> ORGANISM: Artificial Sequence
<220> FEATURE:
<223> OTHER INFORMATION: ORF5-R

<400> SEQUENCE: 6

cacctttagg gcatatatca t                                    21
```